Figure 1:
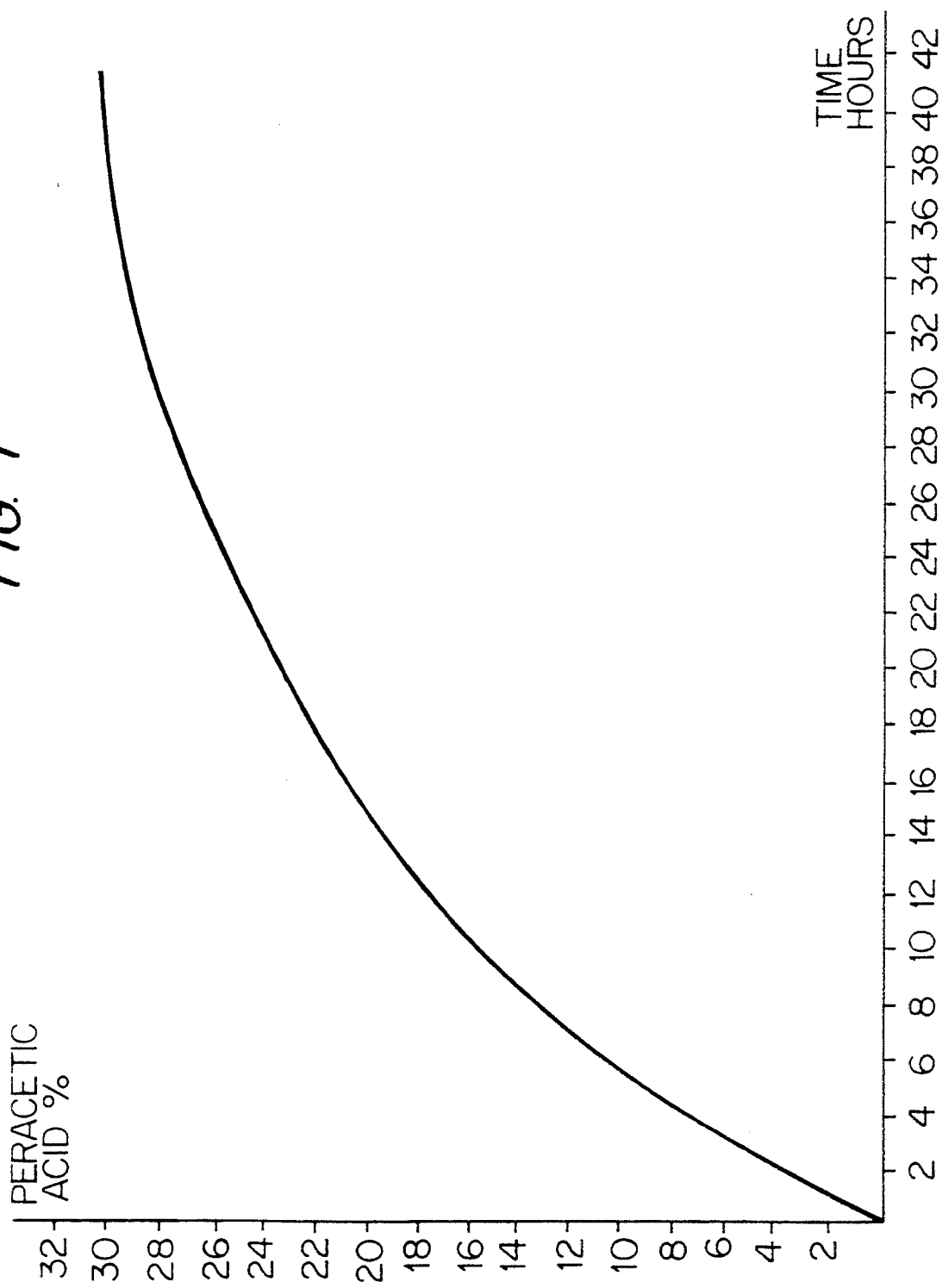

United States Patent

Brougham et al.

[11] Patent Number: 5,349,083
[45] Date of Patent: Sep. 20, 1994

[54] SOLUTIONS OF PERACIDS

[75] Inventors: Paul Brougham, Rainhill; William R. Sanderson, Penketh; Timothy Pearce, High Legh, all of England

[73] Assignee: Solvay Interox Limited, Warrington, England

[21] Appl. No.: 920,480

[22] PCT Filed: Feb. 18, 1991

[86] PCT No.: PCT/GB91/00241
§ 371 Date: Aug. 24, 1992
§ 102(e) Date: Aug. 24, 1992

[87] PCT Pub. No.: WO91/13058
PCT Pub. Date: Sep. 5, 1991

[30] Foreign Application Priority Data

Feb. 23, 1990 [GB] United Kingdom ............ 9004080.9

[51] Int. Cl.$^5$ ............................................ C07C 279/10
[52] U.S. Cl. ............................................ 562/6; 562/2; 562/3
[58] Field of Search .................................. 562/2, 3, 6

[56] References Cited

U.S. PATENT DOCUMENTS 4,297,298 10/1981 Crommelynck .................. 562/3
4,743,447 5/1988 Le Rouzic ........................ 424/616

Primary Examiner—José G. Dees
Assistant Examiner—Joseph M. Conrad
Attorney, Agent, or Firm—Larson and Taylor

[57] ABSTRACT

A dilute solution of a lower aliphatic peracid such as peracetic acid, having an equilibrium composition, is produced by contacting hydrogen peroxide with a lower aliphatic acid each at initial high concentrations in an aqueous reaction mixture to rapidly form a reaction mixture containing, for example, up to 30% by weight of peracid and diluting the reaction mixture with water and with any required quantities of lower aliphatic acid and/or hydrogen peroxide to reproduce the equilibrium composition of the dilute solution, the process being characterized in that the reaction mixture rich in lower aliphatic peracid is diluted before it has itself reached equilibrium, for example when it contains from 20 to 80% of its potential equilibrated content of peracid. The process provides a quick plant-efficient process for the production of stable dilute lower aliphatic peracid solutions for industrial disinfection purposes or for personal or domestic hygiene use.

16 Claims, 1 Drawing Sheet

SOLUTIONS OF PERACIDS

This invention relates to the production of dilute aqueous solutions of lower aliphatic peracids and to their use as disinfecting solutions.

The lower aliphatic peracids are effective wide-spectrum bactericides which have the particular advantage, in use, of leaving as residues only the corresponding lower aliphatic acids and therefore being particularly suitable for applications which require a non-environmentally-polluting disinfectant. While the lower aliphatic peracids in general are contemplated herein, for example those corresponding to carboxylic aliphatic acids containing 2 to 5 carbon atoms, peracetic acid is particularly envisaged since it is already a commercially important peracid for disinfectant purposes. Where the following description relates to peracetic acid it is understood that the other peracids may be read in substitution therefor provided that the technical context allows it. It is also understood that reference to a lower aliphatic acid includes a reference to the corresponding anhydride where appropriate.

Aqueous solutions of peracetic acid containing up to about 45% by weight of peracetic acid are commercially available. Such solutions may be produced by reacting appropriately concentrated hydrogen peroxide and acetic acid in an aqueous medium in the presence of an acid catalyst which is usually sulphuric acid or other strong mineral acid. The acid catalyst may be present in from about 0.1% to about 5% by weight of the reaction mixture.

Aqueous solutions of peracetic acid represent equilibrium mixtures of the reactants and the reaction products and, under relatively forcing reaction conditions, for example when using one or more of a substantial quantity of catalyst, an elevated reaction temperature and a concentrated reaction mixture, equilibrium may be substantially reached in a relatively short time. When using the strong acid catalyst in from 2% to 5% of the reaction mixture, a temperature of from 30° C. to 50° C. and a concentration of acid above about 20% by weight the reaction mixture may come to equilibrium within hours. For some applications, or where long storage is envisaged, it may not be desirable for there to be catalyst residues in a peracid product particularly, for example, dilute products intended for personal or domestic hygiene use. For many applications dilute solutions of peracetic acid, for example below 5% by weight but often below 2%, for example from 0.1% to 2% by weight, are required. Concentrations of peracetic acid above 0.5% by weight for example from 0.5% to 1% by weight, are particularly effective bactericidally in, for example, toilet cleansing applications. Such dilute peracetic acid solutions may be produced directly by reacting acetic acid and hydrogen peroxide in a suitably dilute reaction medium but equilibrium can take an extremely long time to reach, particularly at the more extreme dilutions envisaged. At peracid concentrations below 1% by weight equilibrium may take a month or more to reach if the reaction is not acid catalysed or a week or more even if the reaction is acid catalysed. This entails a very heavy utilisation of plant and equipment on a large production scale.

If a concentrated equilibrium solution of peracetic acid is diluted with water the equilibrium point of the system is progressively altered, as dilution progresses, in favour of the regeneration of the original reactants. The ageing time taken to attain the new equilibrium point, after dilution, is of a similar order to that required to produce such a dilute solution directly from suitable reactants. Such a diluted solution may be used directly although it is not at equilibrium and is therefore of variable composition in storage. Such non-equilibrium diluted solutions also have a composition dictated by the equilibrium point applying at the original concentration, which may not be desired in some applications.

In 1955 Greenspan et al.(Proc. 42nd Ann. Mtg. Chem. Spec. Man. Ass. Dec. 1955), disclosed that stable dilute peracetic acid solutions can be prepared by the use of peracid stabilisers in conjunction with proper adjustment of the relative concentrations of the components of the dilute peracid solution, that is to say that, if the prepared dilute solution is not fully at equilibrium, adjustment of the balance of the components can achieve stability. The solutions in question may be prepared by dilution of commercial, e.g. fully equilibrated peracetic acid which has been produced by the use of small amounts of a mineral acid catalyst.

U.S. Pat. No. 4,297,298 describes the production of an aqueous solution of a lower aliphatic peracid by preparing in a first process step a concentrated solution of the peracid from the corresponding carboxylic acid or anhydride and concentrated hydrogen peroxide in the presence of a small quantity of a strong acid catalyst and diluting the solution with a solution containing at least one of the reagents from the first process step so as to bring the concentration of the aliphatic peracid to the rated concentration of the mixture the concentration of the diluent reagent or reagents being chosen "so that once dilution has been brought about, the system is no longer at equilibrium, but tends to move in the direction of forming further aliphatic peracid at a very slow rate." The process specifically described in U.S. Pat. No. 4,297,298 produces a non-equilibrium composition which contains an extremely high concentration of hydrogen peroxide, e.g. from 28% to 46%. Such a concentration on contact with the user would cause skin bleaching and pain.

U.S. Pat. No. 4,743,447 describes the production of solutions having a hydrogen peroxide base for disinfecting contact lenses, the solution having from 0.005% to 0.1% by weight of peracetic acid, 1% to 8% by weight of hydrogen peroxide and sufficient acetic acid for the system to reach equilibrium. Such a solution may be prepared by direct reaction using a very dilute reaction mixture with lengthy equilibration or from a stable commercial solution having a "weak concentration" of peracetic acid to which the other constituents of the composition are added. This teaching does not therefore avoid the separate initial step of producing a stable weak solution of peracetic acid from which to produce in turn the final product.

It is an object of the present invention to produce a dilute solution of peracid having an equilibrium composition and being relatively stable by a plant-efficient process which does not involve any long equilibration stage or intermediate process step, even without the use of a catalyst.

The present invention provides a process for the production of a dilute solution of a lower aliphatic peracid having an equilibrium composition by contacting hydrogen peroxide with a lower aliphatic acid each at each initial high concentrations in an aqueous reaction mixture thereby to rapidly form a reaction mixture rich in the lower aliphatic peracid and diluting the reaction mixture with water and with any required quantities of lower aliphatic acid and/or hydrogen peroxide to reproduce the equilibrium composition of the dilute solution the process being characterised in that the reaction mixture rich in lower aliphatic peracid is diluted before it has itself reached equilibrium.

The initial concentration of the lower aliphatic acid in the reaction mixture is preferably from 25% to 70% by weight. The initial concentration of hydrogen peroxide in the aqueous medium is preferably from 15% to 35% by weight with the proviso that at least some water is present. The desirability of not using hydrogen peroxide having a concentration above about 86% by weight, more concentrated solutions being hazardous, indicates a minimum quantity of water. Preferably water is initially present in from 15% to 50% by weight. Hydrogen peroxide and peracid concentrations are quoted herein as 100% material unless stated otherwise.

By a reaction mixture rich in lower aliphatic peracid is meant one in which the concentration of peracid is greater than in the equilibrium dilute solution to be finally produced.

The progression of a reaction between acetic acid and hydrogen peroxide to equilibrium, catalysed by an addition of sulphuric acid, is shown in FIG. I, the % of peracetic acid being plotted against time in hours. It is seen that the last few percentage points of the peracid concentration in the reaction mixture takes a substantial proportion of the reaction time to produce. According to the invention the reaction mixture is preferably diluted when it contains from 2% by weight to 30% by weight, particularly preferably to about 25% by weight, of peracid. Alternatively or additionally the reaction mixture rich in lower aliphatic peracid is preferably diluted when it contains from 20% to 80% of its potential content of peracid, having regard to the initial composition of the reaction mixture and the equilibrium applying at the relevant concentration.

In the course of the reaction to produce the reaction mixture rich in lower aliphatic peracid the reaction mixture may be diluted with water to produce an equilibrium composition. If this dilution is performed at a relatively early stage of the reaction, for example when it contains from 20% to 50% of its potential content cf peracid, or when it has a content of peracid of from about 2 to 10% by weight a diluted product having a peracid concentration of about 0.5 to 1.5% may be produced. This is the least time-consuming embodiment of the present invention to operate.

Alternatively the reaction mixture rich in lower aliphatic peracid may be diluted also with lower aliphatic acid and with hydrogen peroxide. Preferably this reaction mixture, at the time of dilution, contains from above 10% to 30% by weight of the peracid which may suitably be diluted to produce a solution containing up to about 0.5 to 12.5% by weight of the peracid.

The performance of the invention requires a knowledge of the equilibrium composition of a solution of the peracid having the desired dilution. This may be determined by making such a solution, allowing it to come to equilibrium and conducting appropriate analytical investigations. While this does entail a long equilibration time to produce the soluton to be analysed, it requires to be performed only on a model system.

Similarly the composition of the relatively concentrated solution from which the dilute solution is to be produced requires to be determined or, in the case of concentrated equilibrium solutions, may be available from manufacturer's data. Where the last-mentioned embodiment of the invention is to be operated, as identified above, the reaction time to achieve the required ratio of lower aliphatic acid, to peracid, to hydrogen peroxide needs to be determined since the process is to be operated by adding water at this point but again this can be performed by suitable analytical investigation on a model reaction system.

The following methods may be used to determine the content of various constituents in the solutions of peracid.

Acetic acid

The peracid and free hydrogen peroxide content of the solution are destroyed by refluxing with excess sodium hydroxide and the acidity is determined by titration of the excess sodium hydroxide with hydrochloric acid using a phenolphthalein indicator. The total acidity figure so obtained is corrected for sulphuric acid content where applicable and for acetic acid generated by the destruction of the hydrogen peroxide and the peracetic acid found to be present by the following techniques.

Hydrogen peroxide

The solution is mixed with dilute sulphuric acid cooled with ice. the hydrogen peroxide content is determined by titration with ceric sulphate solution using ferroin as indicator.

Peracetic acid (dilute solutions)

The solution is mixed with a solution of sodium iodide in ethanediol at $-10°$ C. and the liberated iodine is titrated with sodium thiosulphate solution.

Peracetic acid (concentrated solutions)

The hydrogen peroxide is titrated as above. A potassium iodide solution is added and a titration with sodium thiosulphate solution conducted.

The present invention is particularly suitable for the production of disinfectant solutions for industrial disinfection or for domestic, e.g. toilet cleansing, use. For such use it is desirable for the peracetic acid content to be at about its minimum effective level of about 0.1% to 2% by weight. The concentration of hydrogen peroxide should preferably be below that at which the operator's skin might be bleached on contact i.e. below about 8%, but sufficient to give an available oxygen content in the composition of about 1% to 3.2%, for example from 2% to 7% by weight. The concentration of acetic acid should preferably be appreciable to facilitate the inclusion of fragrances but below the corrosive level, for example from 2% to 9% by weight. The pH should preferably be greater than 1.5, preferably at least 2.0 for example from 2.0 to 5.0. Such solutions cannot be produced by simple dilution of a concentrated equilibrium solution of peracetic acid with water to give the required final peracetic acid concentration since the content of hydrogen peroxide and/or acetic acid relative to that of the peracetic acid, would be unduly low.

The invention may also be utilised to produce solutions having a higher content of peracid, for example up to 15% by weight, from more concentrated solutions of peracid, for example solutions containing from 20% to 45% of peracid by weight and similar considerations and techniques apply to this as are outlined above.

The invention will now be illustrated by means of the following examples of specific embodiments thereof.

EXAMPLE 1

A reaction mixture was established at ambient temperature comprising 2 l 86% wt. $H_2O_2$, 2.6 l glacial acetic acid, 4 l demineralised water, 0.02 l of a 10% solution of dipicolinic acid in aqueous NaOH and 0.0925 kg of a commercial phosphonate stabiliser product (1-hydroxyethylidene-1,1-diphosphonic acid available under the Trade Name Dequest 2010). Dequest is a Trade Name. This corresponds to a hydrogen peroxide concentration in the total mixture of about 28%, of acetic acid of about 27% and a content of water in the mixture, including that introduced with the hydrogen peroxide, of about 45% by weight.

When the concentration of peracetic acid generated in the uncatalysed reaction mixture reached 3.4% weight (20 hours) the weight ratio for peracetic acid to hydrogen peroxide to acetic acid in the reaction mixture was 1 to 6.8 to 7.2 which corresponds approximately to a known stable composition at the intended dilution. The reaction mixture is diluted at this point by adding to 100 g thereof 200 g demineralised water to bring the peracetic acid concentration to 1.14% and the hydrogen peroxide and acetic concentrations each to about 8%. This solution, which had a pH of 2.0, was stored at ambient temperature for 96 days during which time it was periodically analysed. The peracetic acid concentrations so found are set out in Table 1 below:

TABLE 1

| Time (days) | Peracetic acid % wt |
|---|---|
| 0 | 1.14 |
| 3 | 1.08 |
| 6 | 1.04 |
| 30 | 1.00 |
| 54 | 1.02 |
| 75 | 0.98 |
| 96 | 1.02 |

During the initial period of less than 6 days a certain equilibration had evidently occurred. Thereafter a solution having excellent stability was attained.

EXAMPLES 2 TO 4

A reaction mixture containing the proportions of the components thereof set out below was established:

| | |
|---|---|
| Acetic acid (glacial) | 63.60 parts by weight |
| 70% $H_2O_2$ | 34.00 parts by weight |
| conc. $H_2SO_4$ (1.4%) | 1.3664 parts by weight |
| Dequest 2010 (1%) | 0.976 parts by weight |
| Dipicolinic acid (1%) | 0.976 parts by weight |

The potential peracetic acid content of the reaction mixture is about 30% wt. When the actual peracetic acid concentration had reached 26% wt. after about 24 hours three portions thereof were separately diluted to produce solutions predicted to contain respectively 12.4% wt (Ex 2), 1% wt (Ex 3) and 0.59% wt (Ex 4) of peracetic acid. The dilutions were conducted as follows:

| 12.4% peracetic acid | |
|---|---|
| Quantity of 26% peracetic acid solution | 169.87 g |
| Diluent - demineralised water | 195.42 g |
| Diluent - 70% wt $H_2O_2$ | 102.41 g |
| Diluent - Acetic acid (glacial) | 32.32 g |
| 1% peracetic acid | |
| Quantity of 26% peracetic acid solution | 13.89 g |
| Diluent - demineralised water | 404.55 g |
| Diluent - 70% wt hydrogen peroxide | 41.37 g |
| Diluent - Acetic acid (glacial) | 40.2 g |
| 0.59% peracetic acid | |
| Quantity of 26% peracetic acid solution | 7.78 g |
| Diluent - demineralised water | 419.19 g |
| Diluent - 70% wt hydrogen peroxide | 44.67 g |
| Diluent - Acetic acid (glacial) | 28.36 g |

The diluted solution so obtained were stored at ambient temperature for up to 13 weeks during which time they were periodically analysed. The peracetic acid concentrations so found are set out in Table 2 below:

TABLE 2

| | Peracetic acid % wt | | |
|---|---|---|---|
| Time (weeks) | Ex 2 | Ex 3 | Ex 4 |
| 0 | 12.51 | 1.10 | 0.78 |
| 1 | 11.95 | 1.03 | 0.76 |
| 2 | 11.48 | 1.07 | 0.79 |
| 3 | 11.62 | 1.26 | 0.83 |
| 4 | 11.90 | 1.24 | 0.89 |
| 5 | — | 0.83 | 0.92 |
| 6 | 11.87 | 1.29 | 0.98 |
| 8 | 11.79 | — | — |
| 11 | — | 0.98 | 0.81 |
| 12 | 11.38 | — | — |
| 13 | 11.72 | — | — |

Again, particularly in the cases of Examples 2 and 3 an initial equilibration appeared to occur during the first week after which the solutions showed excellent stability. It may be desirable, however, when practising the present invention, to age the diluted solution for up to 1 week.

We claim:

1. A process for the production of a dilute solution of a lower aliphatic peracid having an equilibrium composition by contacting hydrogen peroxide with a lower aliphatic acid each at initial high concentrations in an aqueous reaction mixture thereby to rapidly form a reaction mixture rich in the lower aliphatic peracid and diluting the reaction mixture with water and with any required quantities of lower aliphatic acid and/or hydrogen peroxide to reproduce the equilibrium composition of the dilute solution, the process being characterised in that the reaction mixture rich in lower aliphatic peracid is diluted before it has itself reached equilibrium.

2. A process as claimed in claim 1 wherein the initial concentration in the reaction mixture of the lower aliphatic acid is from 25 to 70% by weight and of the hydrogen peroxide is from 15 to 35% by weight.

3. A process as claimed in claim 1 or 2 wherein the formation of the lower aliphatic peracid is uncatalysed.

4. A process as claimed in claim 1 or 2 wherein the reaction mixture rich in lower aliphatic peracid is diluted when it contains from 20% to 80% of its potential equilibrated content of lower aliphatic peracid.

5. A process as claimed in claim 1 or 2 wherein the reaction mixture rich in lower aliphatic peracid is diluted when it contains from 2% to 30% by weight of lower aliphatic peracid.

6. A process as claimed in claim 1 or 2 wherein the said reaction mixture is diluted when it contains up to 25% by weight of lower aliphatic peracid.

7. A process as claimed in claim 1 or 2 wherein the reaction mixture rich in lower aliphatic peracid is diluted with water as its composition reaches a point at which the ratio of hydrogen peroxide to lower aliphatic acid to lower aliphatic peracid corresponds to the equilibrium composition of the desired dilute lower aliphatic peracid solution.

8. A process as claimed in claim 1 or 2 wherein the concentration of the lower aliphatic peracid in the reaction mixture at the point of dilution is from 2 to 10% by weight and a dilute lower aliphatic peracid solution having a concentration of from 0.5 to 1.5% by weight is produced.

9. A process as claimed in claim 1 or 2 wherein the reaction mixture rich in lower aliphatic peracid is diluted with water and hydrogen peroxide and/or lower aliphatic acid when it has a concentration of from above 10% to 30% of the lower aliphatic peracid to produce a relatively dilute solution having a concentration of lower aliphatic peracid of from 0.5% to 12.5% by weight.

10. A process as claimed in claim 1 or 2 wherein the lower aliphatic acid is acetic acid and the lower aliphatic peracid is peracetic acid.

11. A process according to claim 1 or 2 wherein the concentration of aliphatic peracid in the dilute solution is not more than 12.5% by weight.

12. A process according to claim 1 or 2 wherein the concentration of aliphatic peracid in the dilute solution is not more than 5% by weight.

13. A process according to claim 1 or 2 wherein the concentration of aliphatic peracid in the dilute solution is not more than 2% by weight.

14. A process according to claim 1 or 2 wherein the concentration of aliphatic peracid in the dilute solution is from 0.1% to 2% by weight.

15. A process according to claim 1 or 2 wherein the concentration of aliphatic peracid in the dilute solution is from 0.5% to 1% by weight.

16. A process according to claim 1 or 2 wherein the concentration of aliphatic peracid in the dilute solution is not more than 1% by weight.

* * * * *